(12) United States Patent
Gellerman et al.

(10) Patent No.: US 7,215,420 B2
(45) Date of Patent: May 8, 2007

(54) OPTICAL METHOD AND APPARATUS FOR DETERMINING STATUS OF AGRICULTURAL PRODUCTS

(76) Inventors: Werner Gellerman, 1360 E. Kensington, Salt Lake City, UT (US) 84105; Robert McClane, 484 H. St., Salt Lake City, UT (US) 84103; Paul S. Bernstein, 6633 Old Mill Cir., Salt Lake City, UT (US) 84121

( * ) Notice: Subject to any disclaimer, the term of this patent is extended or adjusted under 35 U.S.C. 154(b) by 307 days.

(21) Appl. No.: 10/472,010

(22) PCT Filed: Mar. 22, 2002

(86) PCT No.: PCT/US02/08893

§ 371 (c)(1),
(2), (4) Date: Feb. 5, 2004

(87) PCT Pub. No.: WO02/077608

PCT Pub. Date: Oct. 3, 2002

(65) Prior Publication Data

US 2004/0130714 A1  Jul. 8, 2004

(51) Int. Cl.
*G01J 3/44* (2006.01)
*G01N 21/65* (2006.01)
(52) U.S. Cl. .................................. 356/301; 356/72
(58) Field of Classification Search ................. 356/301
See application file for complete search history.

(56) References Cited

U.S. PATENT DOCUMENTS

| 4,532,757 A | 8/1985 | Tutle ............................. 56/328 |
| 4,832,483 A | 5/1989 | Verma .......................... 356/39 |
| 5,253,302 A | 10/1993 | Massen ...................... 382/110 |
| 5,257,085 A | 10/1993 | Ulich et al. ................... 356/73 |
| 5,481,113 A * | 1/1996 | Dou et al. .................. 356/301 |
| 5,576,550 A | 11/1996 | Koppikar ................. 250/459.1 |
| 5,657,120 A | 8/1997 | Smith .......................... 356/301 |
| 5,729,473 A | 3/1998 | Blanc et al. ................ 702/128 |
| 5,751,833 A | 5/1998 | Blit et al. ................... 382/110 |
| 5,764,819 A | 6/1998 | Orr et al. .................... 382/110 |

(Continued)

FOREIGN PATENT DOCUMENTS

JP  4-254744  * 9/1992

*Primary Examiner*—F. L. Evans
(74) *Attorney, Agent, or Firm*—Gifford, Krass, Groh, Sprinkle, Anderson & Citkowski, PC

(57) ABSTRACT

A spectroscopic method, preferably Raman scattering, is used to rapidly determine the general health or stress status of living plants and plant products, including agricultural crops, forests, and harvested fruits and vegetables. In the preferred embodiments, carotenoid levels are used to provide an indication of oxidative deterioration. Based upon the results of the analysis, further action may or may not be taken, for example, in terms of choosing, picking, harvesting or sorting the agricultural product in accordance with the carotenoid level. Concentration levels of an analyte substance can be determined relative to an external standard, to each other, or relative to another substance in the item being analyzed. Carotenoids such as lycopene, beta-carotene, lutein, violaxanthin, neoxanthin, antheraxanthin, and zeaxanthin are determined according to the invention, through other plant components may be analyzed such as other terpenes, polyenes, chlorophyll, proteins, starches, sugars, overall nitrogen levels, flavonoids, and vitamins. The hardware associated with the invention may be field portable or mounted on a piece of equipment such as a harvester or sorter.

30 Claims, 7 Drawing Sheets

U.S. PATENT DOCUMENTS

| | | | |
|---|---|---|---|
| 5,873,831 A | 2/1999 | Bernstein et al. | 600/473 |
| 5,956,413 A | 9/1999 | Oste et al. | 382/110 |
| 6,009,186 A | 12/1999 | Gorretta et al. | 382/110 |
| 6,052,187 A | 4/2000 | Krishnan et al. | 356/364 |
| 6,087,563 A | 7/2000 | DellaPenna et al. | 800/317.4 |
| 6,114,683 A | 9/2000 | Spiering et al. | 250/208.1 |
| 6,151,522 A | 11/2000 | Alfano et al. | 600/473 |
| 6,160,617 A | 12/2000 | Yang | 356/300 |
| 6,184,534 B1 | 2/2001 | Stephany et al. | 250/459 |
| 6,205,354 B1 | 3/2001 | Gellermann et al. | 600/477 |

* cited by examiner

OPTICAL METHOD AND APPARATUS FOR DETERMINING STATUS OF AGRICULTURAL PRODUCTS

FIELD OF THE INVENTION

The invention relates to the determination of the freshness of agricultural crops, products, and forests, and in particular, to the determination of antioxidant content through optical methods.

BACKGROUND OF THE INVENTION

In plants, carotenoids act as accessory pigments in light harvesting, and more importantly, to detoxify various forms of activated oxygen and triplet state chlorophyll that are produced as a result of the excitation of photosynthetic complexes by light.

The dollar value of fruit and vegetable crops are dependent on freshness and quality. In the agricultural product handling and food processing industry, there is currently no precise method of determining fruit and vegetable quality or antioxidant nutrient content which is rapid enough to be useful in a continuous flow environment. The current quality control method for fruit and vegetable handlers typically consists of an expensive and imprecise manual selection process based on the color or shape of the product. An automated quality control process would be very useful.

In the food product industry, carotenoid levels (usually lycopene or beta-carotene) are determined using high-performance liquid chromatography (HPLC). These measurements are made throughout the food processing line to assure quality control of the final product. The delay in obtaining HPLC data, which is not a real-time process, leads to difficulties in identifying problems as they occur. A rapid and objective measurement of post-harvest fruit and vegetable quality would have several commercial applications within the agricultural product handling and food processing industries, especially with an increased interest in nutritionally specific claims for fruits and vegetables, and processed functional foods.

An improved system to monitor the health status of food crops has broad commercial potential in agricultural crop management. Traditional methods of determining crop stress (observation of wilting, change in coloration, etc.) appear after damage has already occurred, and crop yields may not be recoverable. Currently, chemical analysis using HPLC is one of the few means available to get early indications that a plant or crop is under stress. However, this technique is invasive, requiring a sample of plant matter for analysis. HPLC is also expensive, time-consuming, requires user training, and is inconvenient to perform away from a laboratory. Conventionally, plant samples may be taken to an analysis laboratory, adding time and expense to the analysis. The link between measurement and plant sample location also has to be recorded for later interpretation of results. Ambiguous results from an HPLC may result from a variety of factors, such as plant sample contamination, and are then inconvenient to repeat. The present invention allows non-invasive determination of stress and environmental effects on plant health, allowing crop yields to be increased. Hence, a system allowing automated quality control using a rapid or effectively instantaneous analysis technique would be extremely useful.

In U.S. Pat. No. 5,873,831, Bernstein et al. describe a system for measurement of carotenoid levels within the macula and fovea of the eye. However, the characterization of plants is not described.

In U.S. Pat. No. 6,052,187, Krishnan describes a plant analyzer based on fluorescence. In U.S. Pat. No. 5,576,550, Koppikar describes a phytoluminometer using luminescence techniques. In U.S. Pat. No. 6,114,683 to Spiering, a plant chlorophyll content imager is disclosed. However, the use and advantages of Raman scattering are not disclosed in these disclosures.

In U.S. Pat. No. 5,257,085, Ulich et al. discloses a Raman imaging lidar system. However, this system is restricted to short pulses of laser radiation and imaging applications. The identification of carotenoids is not disclosed.

SUMMARY OF THE INVENTION

The present invention uses Raman spectroscopy to provide a new method for rapidly determining the general health or stress status of living plants and plant products, including agricultural crops, forests, and harvested fruits and vegetables. In the preferred embodiment, Raman spectroscopy is used to determine levels of carotenoids, so as to determine plant health, guide specific actions, and to increase the effectiveness of crop and forest management. According to the present invention, carotenoid levels determined in harvested plants are used to provide an indication of oxidative deterioration. Embodiments of the invention provide a novel, non-invasive method of monitoring the antioxidant content of fruits and vegetables, and monitoring the deterioration in quality and freshness as fruits and vegetables are harvested, transported and stored prior to consumption and processing. The present invention enables the automation of quality control in the agricultural product handling and food processing industry.

Embodiments of the plant analysis systems described here are field portable, lower cost, and provide a near real time indication of the oxidative stress status in crops, allowing interventions to be more successfully and economically implemented. Embodiments of the invention allow quality control functions in the food processing and food handling industries to be improved and automated. Fruits, vegetables, and other food products such as tomato paste and ketchup can be monitored. During ripening of tomatoes (and other fruits and vegetables), chlorophyll levels decrease and the concentrations of carotenoids such as β-carotene and lycopene increase. Hence, carotenoid levels can be monitored as an indication of ripening stage. Levels of specific carotenoids, and their ratios to each other and to other plant components, are sensitive to environmental stresses such as temperature, drought, fertilizer levels, UV exposure, herbicide applications, parasites, diseases, solar flux levels and the like. Hence, carotenoid monitoring allows plant stresses to be monitored and remediated.

The methods and apparatus of the present invention provide a non-invasive, rapid, and quantitative determination of the carotenoid levels in living plants and plant products, and further provides diagnostic information related to the health and stress status of living plants, and the degeneration of plant products.

DETAILED DESCRIPTION OF THE INVENTION

As described in U.S. Pat. Nos. 6,205,354, 5,873,831 and 4,832,483, the contents of all of which are incorporated herein by reference, in laser Raman spectroscopy, monochromatic laser light is directed onto a particular material to be tested. A sensitive detection system then detects light returning, or scattered, from the material. The majority of the light returning from the material is scattered elastically at the same wavelength of the original projected laser light. A very small fraction of the light returning from the material is scattered inelastically at a wavelength different from that of the original projected laser light in a manner known as Raman scattering. Raman scattered light is then separated from Rayleigh scattered light with the use of filters, optical gratings, prisms, and other wavelength selection techniques. The energy difference between scattered Raman light and the incident laser light, conventionally represented in wave numbers (cm-1), is related to the vibrational, rotational, or librational states, or combinations thereof, of various molecules in the material being evaluated. Each of the peaks in the resulting Raman spectrum corresponds to a particular Raman active vibration of a molecule or a component thereof. The Raman energy shift is independent of the wavelength of the directed laser light. That is, the energy difference corresponding to the elastically and inelastically scattered light for a particular material remains constant for that material. The characteristic results from Raman scattering can be used to locate, identify and quantify concentrations of a material. The absolute intensities of the resulting Raman peaks are directly related to the concentration of the Raman-active molecules in the material.

Figure 1:
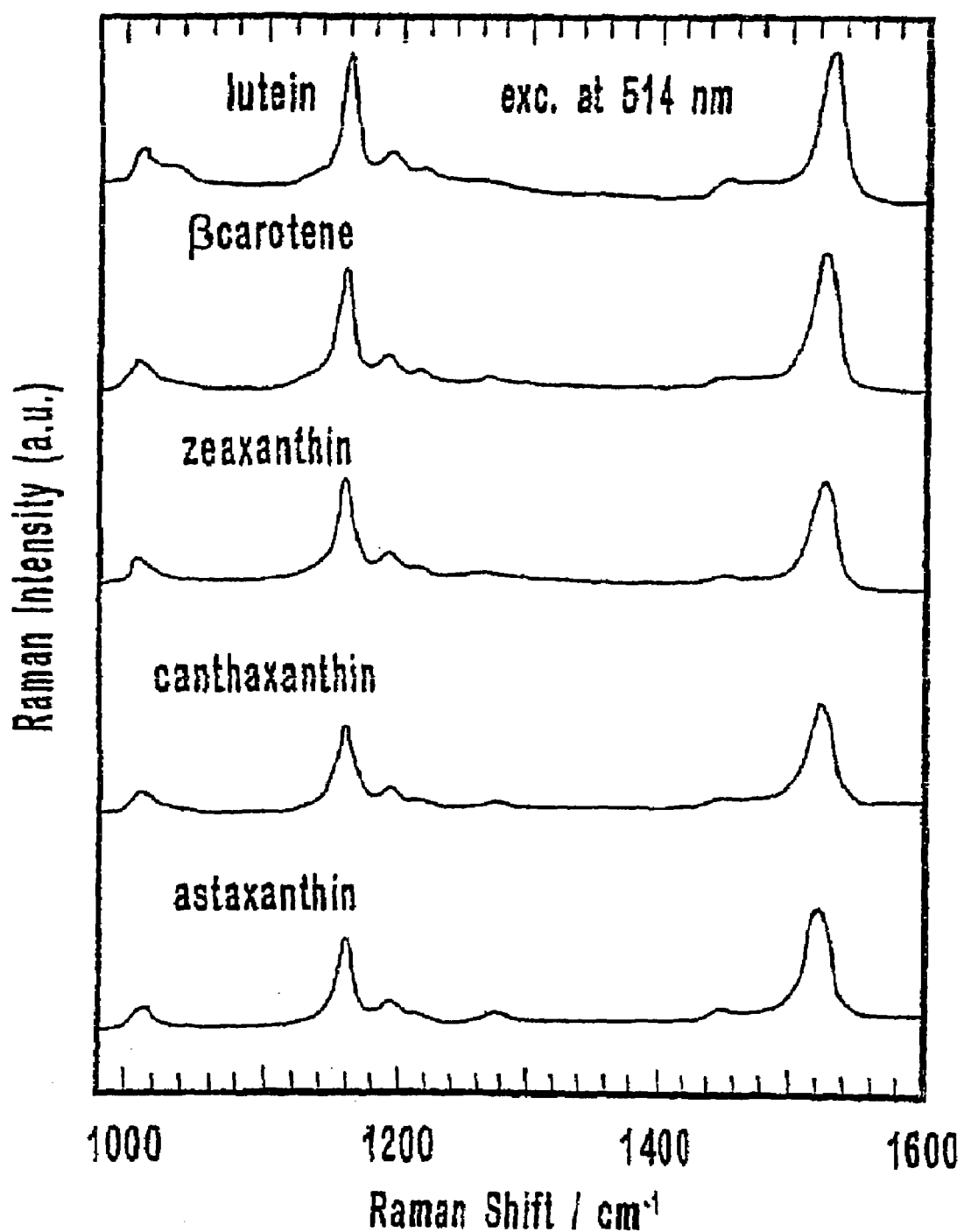
FIG. 1 shows a prior art Raman scattering signals near 1160 and 1520 cm-1, and weaker signals near 1000 cm-1.

Carotenoids, such as lutein and zeaxanthin, have been found to exhibit characteristic Raman scattering, the results of which show up in distinct spectral positions, signal strengths, and spectral widths. More specifically, lutein and zeaxanthin exhibit strong characteristic Raman scattering signals near 1160 and 1520 cm-1, and weaker signals near 1000 cm-1, as illustrated in FIG. 1, which is reproduced from FIG. 1 of U.S. Pat. No. 5,873,831. Further, isolation of any one or all resultant Raman peaks is possible. Additionally, lutein and zeaxanthin demonstrate a resonance Raman scattering amplification when excited by laser light in a range which overlaps with their respective absorption bands, such as from 450 to 550 nanometers.

According to conventional nomenclature, carotenoids are a class of hydrocarbons (carotenes) and their oxygenated derivatives (xanthophylls) consisting of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. However, embodiments of the present invention are applicable to the study of all Raman active molecules. In particular, the present invention is useful in the study of hydrocarbons and molecules containing hydrocarbon groups and chains, the concentrations of which may not be readily detected using other techniques such as IR and fluorescence.

Figure 2:
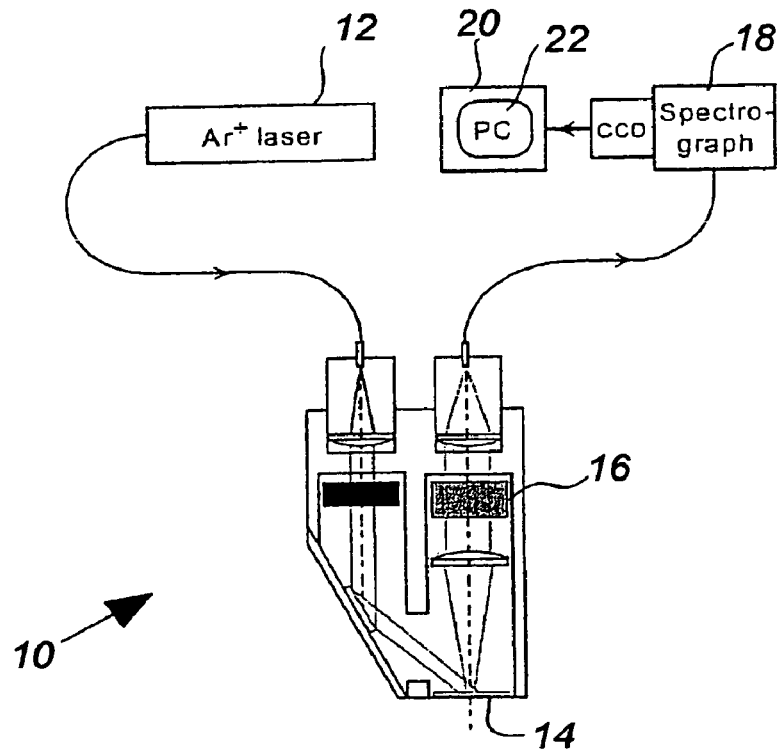
FIG. 2 shows a plant analysis system according to the present invention.

FIG. 2 shows a plant analysis system according to the present invention, shown generally at 10, for determining carotenoid levels within plants. This system may be used in a Raman analysis module used in applications described below. The system 10 comprises a laser 12, a beam diverter 14, a filter 16, an analyzer 18, computer module 20, and display 22. The laser 12 provides a beam which passes (substantially undiverted) through the beam diverter 14 and is incident on portion of a plant 30. Light returns from the agricultural product, be it a plant, produce, or otherwise, where the Raman scattered component is, diverted by the beam diverter 14 through filter 16 to analyzer 18. The beam diverter 14 preferably has wavelength dependent properties, so as to pass light at the laser wavelength undiverted, while diverting the Raman scattered light wavelength of interest.

In a preferred embodiment, beam diverter 14 is a dichroic mirror. In other embodiments, the diverter 14 may be a holographic grating, a prism, a dielectric film or multilayer, a photonic device, other periodic structure, simple mirror, curved mirror, and the like. If diverter 14 is a grating, Raman scattered light is selectively diffracted to the analyzer. The filter 16 transmits Raman scattered light while not allowing the laser wavelength to pass through it. Preferably, filter 16 is a holographic filter (such as a holographic notch filter manufactured by Kaiser Optical Systems of Ann Arbor, Mich.) but other filters may be used. In other embodiments, the filter 16 may be omitted, for example when the beam diverter is sufficiently wavelength selective. In other embodiments, if the filter 16 alone is sufficiently effective in rejecting laser radiation, the properties of diverter 14 can be a simple beam splitter (though this may reduce the signal strength at the analyzer). The diverter 14 may also be used to reject other unwanted radiation, such as sunlight.

After the scattered light is spectrally selected, it is directed to an analyzer 18 which measures the intensity of the scattered light as a function of wavelengths in the region of Raman peaks around 1160 and 1520 cm-1, characteristic of carotenoids (these numbers are for macular carotenoids, and may be adjusted for carotenoids present in particular plant species and products).

The analyzer 18 will be discussed in more detail later, but may be any conventional spectroscopic analyzer. The data from the analyzer 18 are passed to the computer module 20, which then displays results to the operator on the display 22. The analyzer can detect carotenoids using the intensity of a single Raman peak, the intensity ratio of two or more peaks, the intensity ratio of an analytic Raman peak and a reference signal. A polarizer may be incorporated into the detection system, so that the depolarization characteristics of the Raman spectrum can be determined, which may be diagnostic.

In preferred embodiments, the laser light source generates laser light in the 450 to 550 nm range, which corresponds to the absorption characteristics of carotenoids. However, other wavelengths of generated light would be effective with the apparatus of the present invention. In another embodiment, the light collection system may be structurally separated from light delivery system. Scattered light from the plant can also be collected using optical fibers, lenses, mirrors, remote apparatuses, and combinations of the above. For example, scattered light can be collected using a fiber optic bundle or light pipe. Active fibers can be used to optically amplify the collected scattered light for improved sensitivity.

In the preferred embodiment, concentrations of carotenoids such as lycopene, beta-carotene, lutein, violaxanthin, neoxanthin, antheraxanthin, and zeaxanthin are determined within plant materials. However, embodiments of the present invention can be used in analyzing other plant components such as other terpenes, polyenes, chlorophyll, proteins, starches, sugars, overall nitrogen levels, flavonoids, vitamins (such as vitamin A), and other substances (such as those discussed in U.S. Pat. No. 5,955,269 to Ghai et al., incorporated herein by reference). The laser wavelength may be selected according to the absorbance bands of the compound to be analyzed. Compounds may be detected without determination of concentration.

Concentration levels of an analyte substance can be determined relative to an external standard, to each other, or relative to another substance in the item being analyzed. Plant stress can be determined from leaf carotenoid to chlorophyll ratios. Raman scattering can be combined with other techniques, such as optical spectra and fluorescence, so as to determine such ratios. Conversion between carotenoids can also be determined, e.g. using peak intensity ratio determination, for example the de-epoxidation of violaxanthin to antheraxanthin and further to zeaxanthin in the presence of high light levels. Hence, ratio measurements of violaxanthin levels to those of antheraxanthin and/or zeaxanthin are diagnostic of environment effects.

In preferred embodiments of the present invention, the light source generates radiation within an absorption band of carotenoids, for example in the approximate range 450 to 550 nm. A laser is preferred, but other intense light sources may be used. For portable applications, the laser is preferably a semiconductor laser or other solid state laser emitting in the preferred wavelength range, such as an indium gallium nitride laser. A frequency doubled near-IR laser can also be used to obtain the preferred wavelength range. This may be a frequency-doubled semiconductor laser or a rare-earth doped crystal or glass laser, for example a titanium-sapphire laser with an intracavity potassium dihydrogen phosphate frequency doubler. The laser may further be a gas laser, such as an argon ion laser or green helium neon laser. Gas lasers may be inconveniently large for portable applications, but may be advantageously used in fixed installations such as an automatic quality control system (e.g. analyzing products passing by on a conveyor), or a unit to which operatives convey samples periodically for analysis.

In some embodiments, it is advantageous that the laser radiation is modulated or pulsed. Phase sensitive detection techniques can then be used to increase signal to noise ratio, reduce the contribution of fluorescence to the detected signal, reduce the effects of stray light, and the like. The laser may be pulsed so as to reduce the average laser intensity to eye-safe levels. Using a pulsed light source, such as a pulsed laser, the characteristics (intensity and wavelength shift) of Raman scattered light can be determined from a time-dependent analysis of detected scattered light. Pulsed light emitting diodes can be operated at higher output levels, as described in U.S. Pat. No. 6,184,534.

In a preferred embodiment, the analyzer is a grating monochromator. In other embodiments, a dispersive element can be used to direct scattered light to a plurality of detector elements, such as an array. The detector elements can be positioned relative to the dispersive element so as to receive light at Raman frequency shifts characteristic of carotenoids. In other embodiments, holographic filters are used to selectively pass Raman scattered light to one or more detectors, or detector arrays such as CCD (charge coupled device) cameras. The Raman scattered light has a wavelength shift, relative to the laser, characteristic of the substance of interest. Any extraneous, or stray, light, coincidently at the same wavelength, will also be passed by the filters. Hence, it is advantageous to minimize stray light. The characteristics of the Raman scattered light (such as intensity level, intensity ratio of two Raman peaks, polarization data, wavelength, are then determined. A reference signal may be provided so that a measured intensity is normalized by the reference signal. The presence and concentration of the substance of interest in the subject under study is hence determined from the characteristics of the Raman scattered light.

Figure 3A:
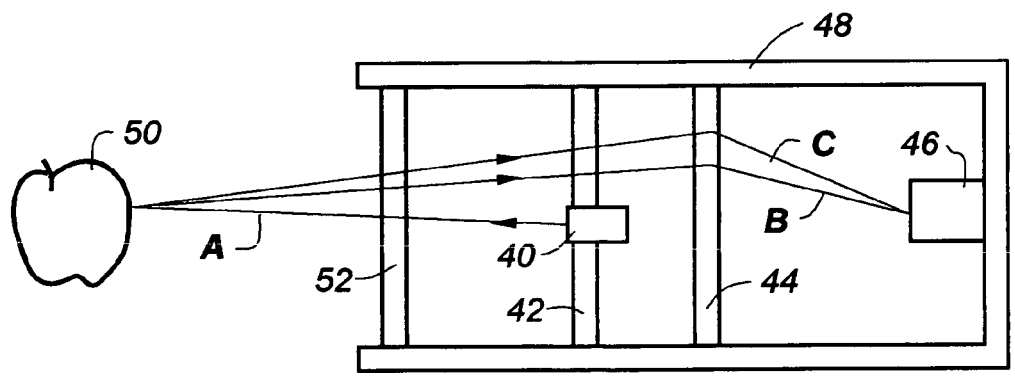
FIG. 3A shows in cross-section view another embodiment of a device according to the present invention.

FIG. 3A shows another embodiment of a device according to the present invention, in cross-section view, comprising a laser 40, filter 42, Fresnel lens assembly 44, analyzer 46, housing 48, and window 52. Laser light emitted by laser 40 (shown as beam A) is incident on plant part 50, and a portion of the scattered light returns so as to be incident on filter 42 (illustrated by beams B and C). The Raman scattered light is selectively transmitted through the filter, and directed by the lens 44 to an analyzer 46. The filter 42 has a toroid shape. A computing module and display may be also be incorporated with the housing, or the device may be used with a separate computing device such as a lap-top. Other lenses, mirrors, prisms, and the like can be used to direct collected scattered light to the analyzer 46. For example, in other embodiments, the window 52 can comprise the functionality of a lens, and the lens 44 omitted; or alternatively the filter 42 can be combined with both window and lens functionalities, so that lens 44 and window 52 can be omitted. Scattered light is collected over a range of backscattering angles using the lens (or mirror) assembly, so as to increase the intensity of scattered light at the analyzer.

Figure 3B:
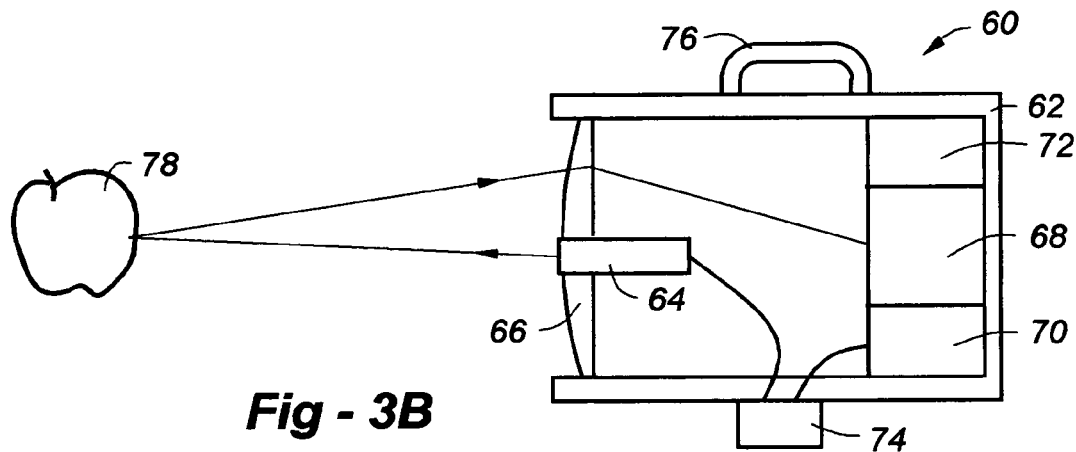
FIG. 3B shows a cross-section of a further embodiment of a device according to the present invention.
Figure 3C:
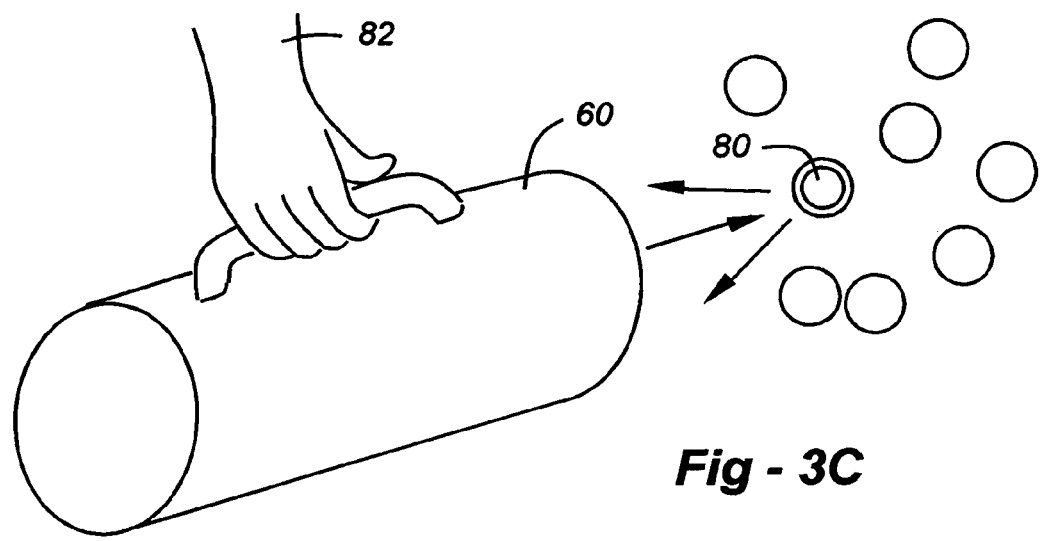
FIG. 3C shows a person holding the device illuminating a fruit or vegetable display.

FIG. 3B shows a cross-section of another embodiment of a device according to the present invention, a Raman analysis module shown generally at 60, comprising a housing 62, a laser 64, combined lens/filter 66, analyzer 68, power supply 70, switch 74, computing module 72, and handle 76. The device can further comprise a display and data entry mechanism. FIG. 3C shows a person 82 holding the device 60 so as to illuminate a fruit or vegetable display 80. In a grocery store environment, an employee can move ripening produce towards the front of the display.

Figure 4:
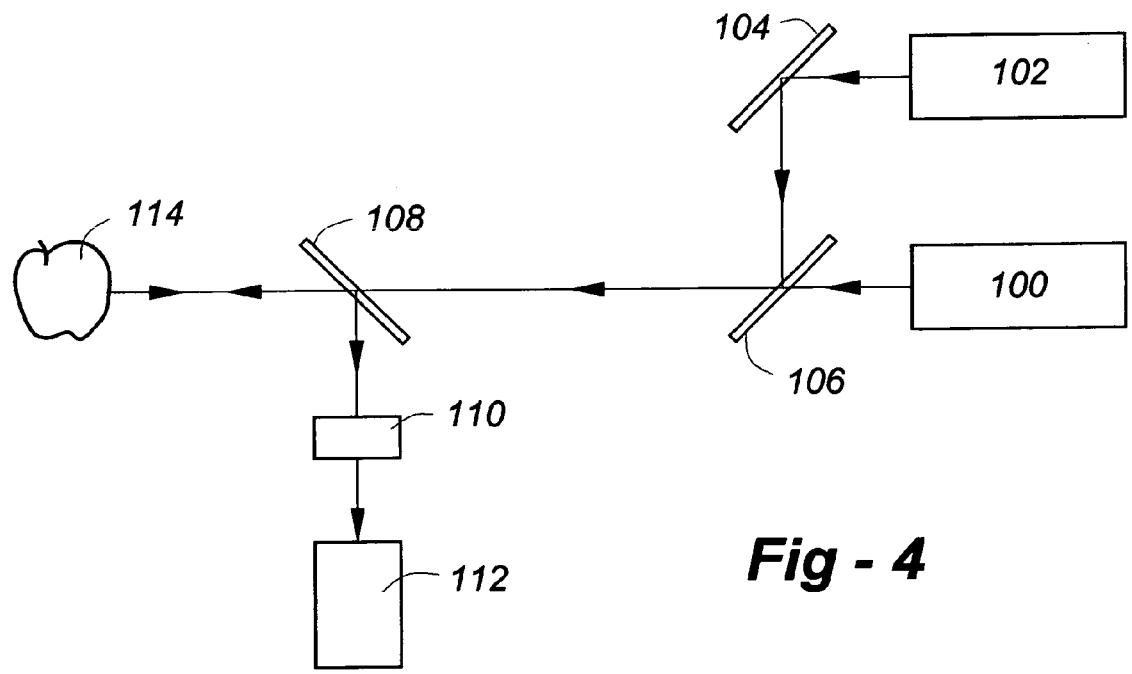
FIG. 4 shows a system in which multiple laser beams are incident on a plant sample.

FIG. 4 shows a system in which multiple laser beams are incident on a plant sample 114. The system comprises a first laser 100, a second laser 102, a reflector 104, a beam splitter/combiner 106, a beam diverter 108, a filter 110, and an analyzer 112. System elements 102, 104, and 106 allow a second laser wavelength to be incident on the plant part, allowing non-linear Raman enhancements to increase the signal strength, as is known in the art. Other system elements have the function of the analogous components described with respect to FIG. 1. The principles of conventional nonlinear Raman spectroscopics are described by Afano et al. in U.S. Pat. No. 6,151,522, incorporated herein by reference.

Figure 5:
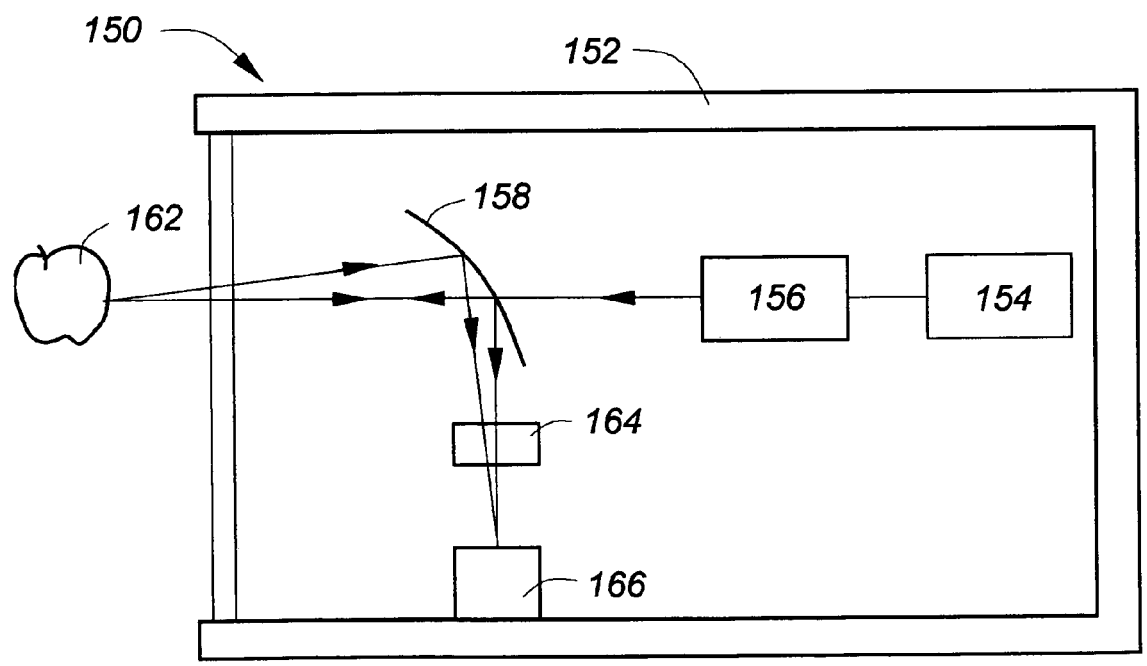
FIG. 5 shows an example of a hand-held device according to the present invention.

FIG. 5 shows an example of a hand-held device, shown generally at 150, according to the present invention, comprising a housing 152, laser 154, beam conditioner 156, mirror 158, window 160, filter 164, and analyzer 166. In this example, the laser is a semiconductor laser, such as an indium gallium nitride laser, and the beam conditioner is included to improve the spatial and spectral qualities of the beam. The beam conditioner may be simply a lens, an aperture, a combination of elements, or a system adapted from the disclosure of Smith in U.S. Pat. No. 5,657,120, incorporated herein by reference, in which the beam passes through a grating, and an aperture is used to select a grating order so as to eliminate laser sidebands. The Raman signal is obtained from a portion of a plant 162 on which the laser beam is incident. The window 160 is used to seal the housing, while allowing beams in and out of the device. The window can have optical filter functionality, so as to reduce extraneous light, IR, and the like. The device may have an internal battery, or be powered by an external power source such as a car battery, mains electricity, and the like.

Figure 6:
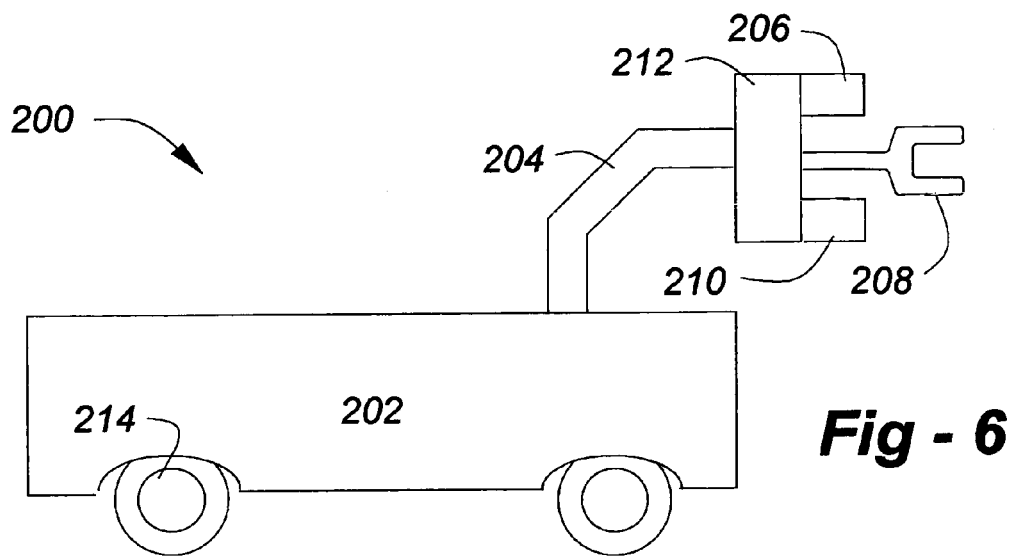
FIG. 6 shows a harvesting machine.

FIG. 6 shows a harvesting machine shown generally at 200 having a mobile body 202 (on wheels 214), an articulating arm 204, image sensor 206, grippers 208, Raman analysis module according to the present invention 210, a control module 212 having a processor adapted to analyze the image sensor data to identify fruit (or vegetables) and signal from the Raman module, so as to grip and pick only suitable fruit, as determined from Raman data and image analysis.

A plant analysis module according to the present invention allows improvement of conventional robotic harvesters, for example as described by Gorretta et al. in U.S. Pat. No. 6,009,186 and by Tutle in U.S. Pat. No. 4,532,757, incorporated herein by reference, by enabling the harvesting system to only select plant parts having desired characteristics (for example, fruit or vegetable ripeness state). A fruit can be identified using conventional techniques, then analyzed by a plant analysis module according to the present invention, so as to determine its characteristics before harvesting. Alternatively, fruit can be analyzed periodically during harvesting for quality control purposes. The conventional fruit harvester of U.S. Pat. No. 4,532,757 is preferably operated at night due to problems with leaf reflections, a problem which may be overcome using embodiments of the present invention.

Figure 7:
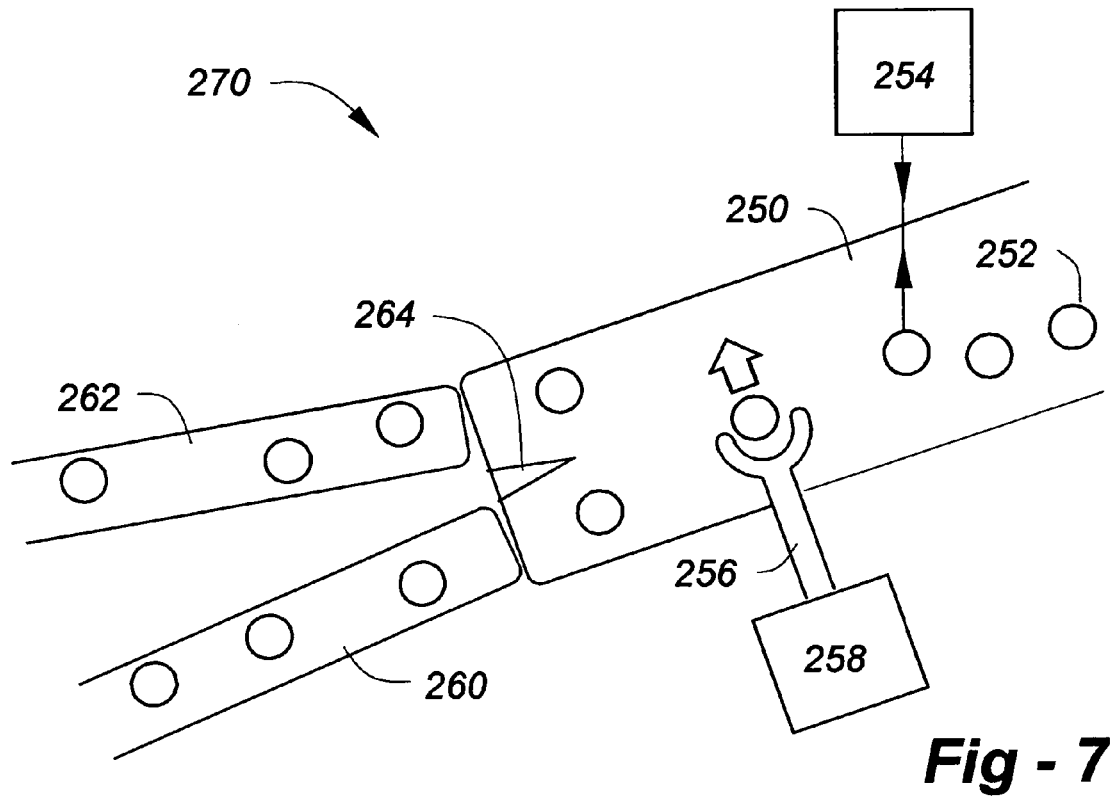
FIG. 7 shows a fruit sorting system comprising conveyor belt carrying fruit.

FIG. 7 shows a fruit sorting system (which can also be used for vegetables and other products) shown generally at 270 comprising conveyor belt 250 carrying fruit 252. The fruit are irradiated by the laser beam (A) from Raman analysis module (according to the present invention) 254. The module or the beam from the module may be moved laterally across the conveyor belt if necessary. A signal from the module 254 is sent to a controller/actuator 258 of the fruit moving arm 256, which pushes high carotenoid level fruit across the conveyor, so as to send the fruit along second conveyor 262, instead of default conveyor 260. The arm is downstream (in terms of conveyor motion) from the Raman analysis module, allowing time for the collected data to be analyzed and a signal sent to the actuator/controller 258. A partition 264 helps direct fruit along the appropriate belt. Other variations of this system will be clear to those skilled in the engineering arts. High antioxidant fruit (or vegetables) may then be sold at a premium over regular fruit, allowing a business method to be developed based on the Raman scattering systems and methods of the present invention.

Embodiments of the present invention can be incorporated into conventional product sorting equipment, such as described in U.S. Pat. No. 5,729,473 to Blanc et al., U.S. Pat. No. 5,956,413 to Oste et al., and U.S. Pat. No. 5,751,833 to Blit et al., the contents of all of which are incorporated herein by reference. Improved product sorting systems are enabled, allowing products to be sorted according to carotenoid levels, facilitating handling, bruising predictions, separating of premium product, elimination of undesired product, and the like. An image processing system can be used to guide the laser beam of the plant analysis module to product on, for example, a moving belt. Alternatively, the belt may be narrow, grooved or dimpled so as to order the product for automatic analysis.

Figure 8:
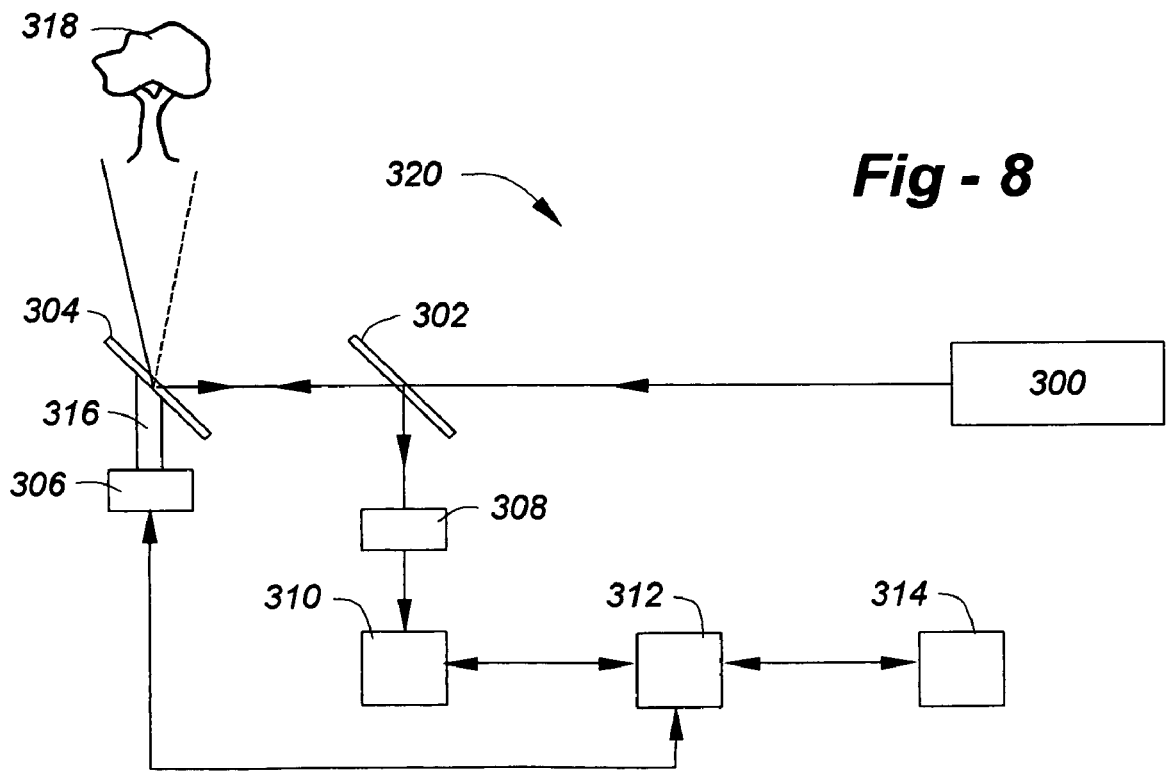
FIG. 8 shows a scanning Raman analysis module.

FIG. 8 shows a scanning Raman analysis module, shown generally at 320, comprising laser 300, beam diverter 302, output scanning mirror 304, mirror driver 306, filter 308, analyzer 310, computer module 312, display 314, and mirror support arm 316. The mirror driver 306 induces deflections of the mirror through motion of arm 316, so as to allow the projected laser beam to be scanned in one or more dimensions over an object. FIG. 8 shows a tree 318 being scanned. Beam scanning can be in a raster mode, point to point (for example based on image analysis of the target object), or vector scanning over a predetermined path. The computer module 312 may be used to reconstruct a Raman image of the target object, so as to determine spatial variations in carotenoid levels, and show them on display 314.

The scanning of the laser beam may be controlled by software using image analysis, for example using data from an imaging sensor, so as to guide the laser beam to the plant parts of interests.

FURTHER APPLICATIONS

Embodiments of the present invention can be supported by aircraft flying over a crop or forest. The health status of a forest can be evaluated from the carotenoid levels in the forest canopy, and the onset of stress problems in crops can be detected using the present technique early enough for remedial action, such as watering, fertilizing, the application of a herbicide or pesticide, and the like, to be taken. Remote sensing systems and methods, such as disclosed by Orr et al. in U.S. Pat. No. 5,764,819, incorporated herein by reference, can also be adapted for use with a plant analysis module of the present invention. A Raman scattering based plant analysis method, according to the present invention, can be used in plant breeding programs (such as chile pepper breeding) so as to select plants with desired characteristics such as high carotenoid levels.

Portable devices can be carried into a field and placed against, in proximity, or otherwise in line of sight view of the plant part of interest, and the laser emission directed against the plant part so as to receive scattered radiation back from the plant. Portable devices may further comprise a global positioning system and compass so as to identify the location and orientation of the device. A rangefinder can be used to determine distance to a plant part. Environmental sensors, such as temperature, humidity, and pressure sensors, may be included so as to compensate for the effect of environmental conditions on detected data. A photocell may be included so as to measure solar flux levels for compensation of data and record keeping. Weather data, and other data, may be entered into system embodiments using a data entry mechanism such as an array of buttons.

The Raman experimental technique can be combined with other analysis methods, such as UV, visible, and IR spectra, IR emission (thermal imaging), fluorescence, photoacoustic spectra, ultrasound, other spectroscopic techniques, visual appearance, feel, smell, and with other invasive analysis techniques such as HPLC, other chromatography methods, and consumption by a human, animal, bacteria or other life form. For example, embodiments of the present invention can be combined with the portable fluorescence based plant analyzer of Krishnan et al., U.S. Pat. No. 6,052,187, incorporated herein by reference.

Embodiments of the present invention can further be used in: selective fruit, vegetable, or salad picking, for example, so as to allow selection of optimum ripeness fruit for picking and transport; fruit or vegetable packing, for example so as to allow damaged or over-ripe fruit to be rejected; plant harvesting; determination of crop treatments to optimize a harvest; in plant breeding and genetic engineering so as to identify plant strains with high or low antioxidant levels; analyzing quality of stored materials, with possible feedback control of storage conditions and alerts if problems are detected; controlled ripening of harvested crops such as tomatoes, for example under various ripening treatments such as ethylene gas, for example by monitoring levels of lycopene; evaluating the freshness of displays such as fruit displayed in grocery stores, salad bars, and the like; controlling the growing conditions of plants such those as in a greenhouse, hydroponics system, or other controlled irrigation and fertilizing environment, through feedback control of watering and fertilizer applications; determining the effects of acid rain, climate change, and other environmental stresses on plant life; measuring the fresh fruit content of fruit juices and their mixtures and blends; characterization of neutraceuticals; characterization of processed foods and products such as jams, preserves, pet foods, baby foods, vitamin products, tomato products, dietary supplements, and the like; quantitative prediction of leaf color changes, for example for tourism purposes; forestry; identification of pollutant spread through detection of plant stress; characterization of seeds, cereals, grains and the like; characterization of liquids, such as health drinks or liquid meal replacements; measurement of vitamin levels in produce (fruits and vegetables) and other food products, including those fortified with vitamins, in particular vitamin A concentrations in e.g. milk; characterization of food additives such as food coloring; pigment production; spice and neutraceutical characterization; herbicide and pesticide research; grape and wine production; algal bloom characterization; evaluation of effects of hot and/or cold temperatures on crops, natural oil characterization (e.g. carotenoid rich oil (such as palm oil) concentration in a blend); characterizing the effect of UV exposure and upper atmosphere ozone depletion on plant stress; nutritional supplement quality control (such as to limit levels of carotenoids to non-toxic levels); in micro-Raman systems; and the like.

A conventional plant screening system, such as described in U.S. Pat. No. 5,232,302 to Massen, incorporated herein by reference, can be improved by adaptation to include a plant analysis module according to the present invention. Plants, fruits, vegetables, and the like with desired characteristics can be selected using such a system.

Multiple laser beams of the same wavelength can be directed at the same plant part so as to increase the scattered intensity. In some cases, a portion of rind, bark, skin, or other covering will be removed from a product so as to expose a region of interest for analysis. The laser wavelength may be chosen so as to be transmitted by such a covering. One or more optical fibers can be used to deliver Easer radiation and collect scattered radiation. Embodiments of the present invention may be provided with a probe structure so as to be inserted into a plant product. For example, this may be a hollow needle through which laser radiation and scattered radiation are guided. In other embodiments, scattered light is interpreted by an analyzer module remote from the laser, and the analyzer module transmits Raman data to a remote operator. For example, the remote operator may aim a laser beam at a remote sample, scattered light from the sample is spectrally filtered and the Raman components analyzed, and a signal transmitted back to the operator using any convenient method. An analysis system according to the present invention may further comprise: a scraper to expose a material of interest; a fluid extractor, using e.g. suction; a sample holder, such as a slot, indent, grippers, and the like, or a tube containing fluid for analysis; liquefying and straining mechanisms; an adapter to make optical coupling with another apparatus, such as a pipe; a marker to indicate items tested; and the like.

Embodiments of the present invention can also be used for studying other living organisms, such as photosynthesizing organisms (including algae) discussed by Yang in U.S. Pat. No. 6,160,617, incorporated herein by reference. Embodiments of the present invention can further be used to in quality control of eggs and egg products.

Stresses in cereal crops that would lead to a decline in yield can be identified by studies of the leaves using systems and methods of the present invention, and remedial action taken to maintain crop yield.

Preferably, the laser intensity is limited so as to not damage the item under analysis, or to substantially change the concentration of the analyte substance.

Other optical techniques can be used to characterize the status of plant material, including other vibrational spectroscopes, laser-induced fluorescence, and optical absorption spectra.

HPLC CORRELATION STUDIES

A wide variety of fruits and vegetables were studied to represent a diverse range of qualitative and quantitative levels of different carotenoids, and are listed in the following Table 1:

TABLE I

| Fruits and vegetables (includes juices) | Main Carotenoids |
| --- | --- |
| Tomato | Lycopene, β-carotene, lutein |
| Carrot | β-carotene, α-carotene |
| Spinach | Lutein, zeaxanthin, β-carotene |
| Orange | β-carotene, cryptoxanthin, lutein, α-carotene |
| Beet leaves | Lutein, zeaxanthin |
| Lettuce | Lutein, zeaxanthin |
| Pepper (red, green, yellow, orange) | Lutein, zeaxanthin, β-carotene |
| Strawberry | β-carotene |
| Guava | β-carotene |
| Grapes | β-carotene, lutein, α-carotene |
| Black Berry | β-carotene, lutein, α-carotene |

Chemical Extraction Procedures for Carotenoids in Fruits and Vegetables

All extraction work was done in the dark or in subdued light. Approximately one hundred-mg of fruit and vegetable tissues were extracted in the presence of 2 ml cold, oxygen-free acetone [Containing 0.1% (w/v) butylated hydroxy toluene (BHT) to avoid promotion of epoxides]. Acetone was chosen as the preferred solvent as it was miscible in water and also it dissolves protein-carotenoid-lipid complexes rather easily. The samples were crushed in mortar and pestle until it became colorless. Ten subsequent acetone extracts were pooled and centrifuged to remove insoluble material. Whenever required (especially in case of green vegetables), aliquots of the extracts (20 ml) were treated with 10 percent methanolic potassium hydroxide solution 2 ml and kept at 4° C. for complete saponification of xanthophyll esters.

The combined acetone extract was transferred to a 50 ml centrifuge tube; 5 ml of n-hexane (cold and oxygen-free) was added to it and mixed gently (gentle mixing avoids emulsion formation). Five-ml cold distilled water was also added to the mixture to cause phase separation. If necessary, a few drops of saturated NaCl solution were added to break the emulsion. The pigments were concentrated by vacuum evaporation (speed vac) and then stored at −20° C., before analysis. The pigments were reconstituted in a suitable solvent (normally HPLC mobile phase) for HPLC analysis. The volumes of solvents were adjusted proportionately. Pigment extraction from the fruits and vegetables juices was achieved using one ml aliquot of the fruit juice as starting material.

HPLC Measurements on Fruit Extracts

Since high-performance liquid chromatography (HPLC) is the current standard for carotenoid analysis, we investigated HPLC detection in our samples. The HPLC equipment (Thermo Separation Products Inc. U.S.A.) featured a four-channel solvent degasser SCM 1000, a binary low pressure gradient pump P4000, a UV-Visible Photodiode array detector, autosampler and Chromquest chromatography software. Different mixtures of HPLC-grade solvents procured from Fisher Scientific were studied as mobile phases at a flow rate 0.7 ml/min. The column was maintained at room temperature. The HPLC detector was operated at 450 nm for quantitation purpose, subsequently. Peak identities were confirmed by photodiode-array spectra and by coelution with authentic standards as necessary. The optimal chromatographic conditions are shown in Table 2. System A was used for estimation of β-carotene and lycopene content, and system B was employed for the estimation of lutein and zeaxanthin. Quantitation was based on the area under the corresponding peaks. A graph of standard carotenoid concentration (mg/l) and peak area was plotted. Samples were diluted whenever necessary to bring the response into the detection range of the instrument.

TABLE 2

| Parameter | Conditions |
| --- | --- |
| HPLC system A, Isocratic RP Column | Microsorb (25 cm length × 4.6 cm id) $C_{18}$ column (Rainin Instrument Co. Woburn, MA, U.S.A. |
| Mobile phase (v/v) | Acetonitrile: 2-Propanol: Ethyl acetate (75:15:10). |
| Flow rate | 0.7 ml/min |
| HPLC system B Column | Microsorb (25 cm length × 4.6 cm id) Cyano column (Rainin Instrument Co. Woburn, MA, U.S.A. |
| Mobile phase (v/v) | Hexane: dichloromethane: methanol: N,N'-di-isopropylethylamine (80:19.4:0.5:0.1) |
| Flow rate | 1.0 ml/min |

Stock solutions of carotenoids standards were prepared in hexane. Concentrations of the standard solutions were checked spectrophotometrically using the corresponding extinction coefficient reported values in the standard (see, Methods in Enzymology, Carotenoids Part A, Chemistry, Separation, Quantitation and Antioxidation 213 (Ed: Packer, L.); Academic press). Aliquots were evaporated to dryness in an argon stream and the residues were dissolved in the mobile phase and subjected to HPLC analysis. Standard calibration graphs were prepared for carotenoids by plotting peak area measurements at 450 nm versus concentration. Linearity, reproducibility and recovery were determined routinely.

Figure 9:
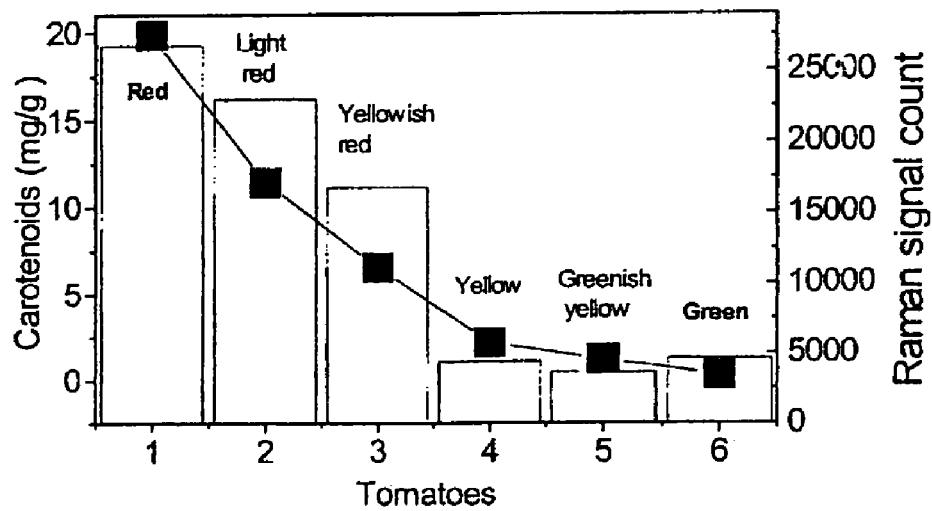
FIG. 9 shows the relation between carotenoid content of tomatoes at different ripening stages and Raman count (bar box) of the diluted extract taken in organic solvent (acetone) recorded at 488 nm.
Figure 10:
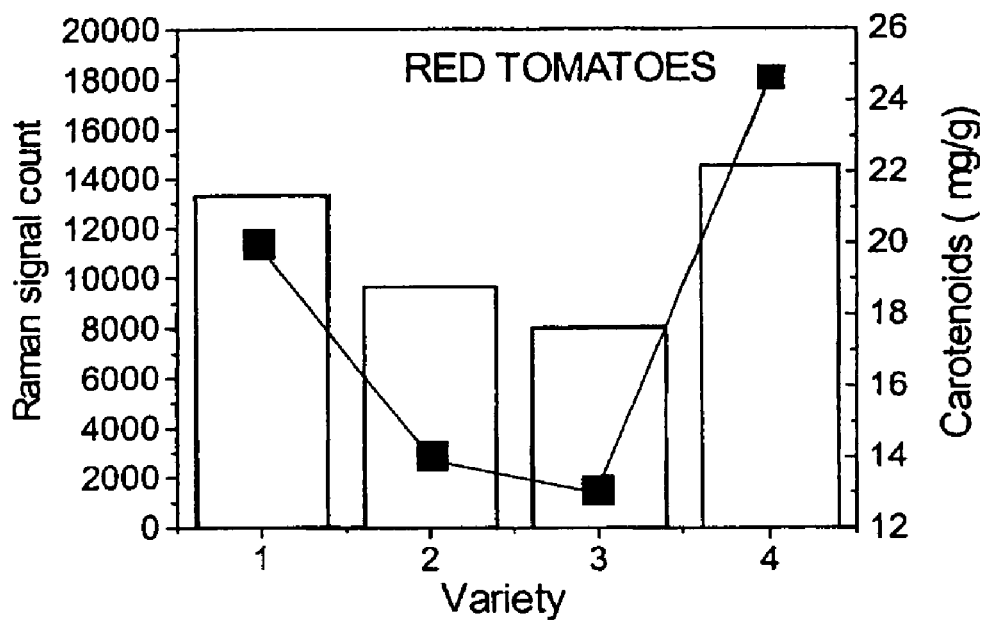
FIG. 10 shows the relation between carotenoid content of ripe red tomatoes of different varieties and Raman count (bar box) of the tomato recorded at 488 nm excitation.
Figure 11:
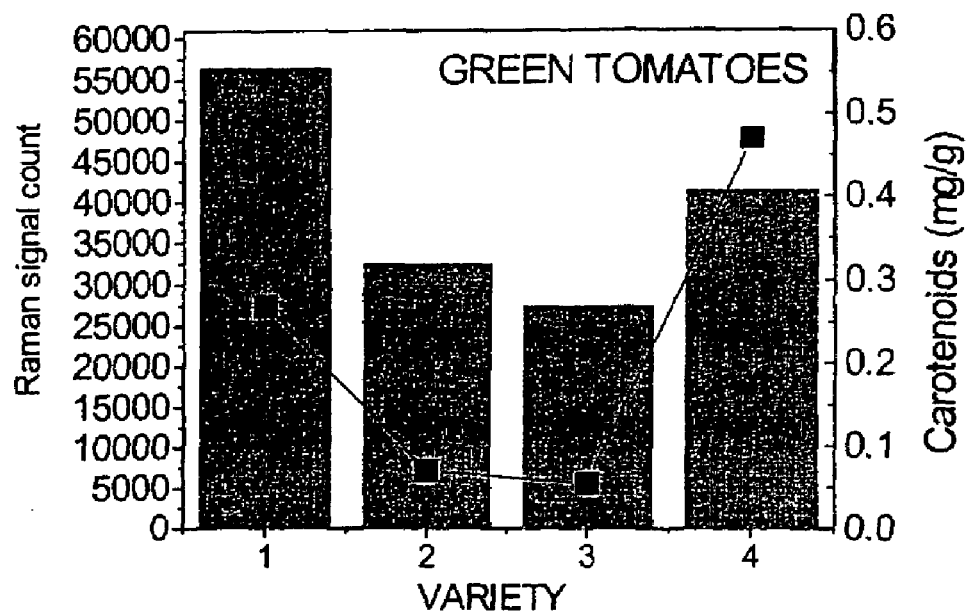
FIG. 11 shows the relation between carotenoid content of unripe green tomatoes of different varieties and Raman count (bar box) of the tomato recorded at 488 nm excitation.
Figure 12:
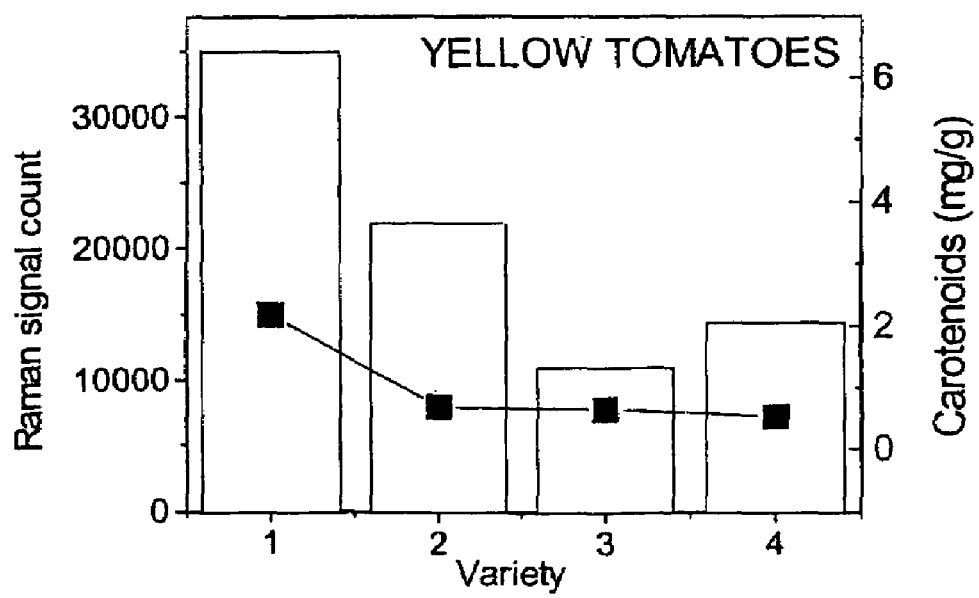
FIG. 12 shows the relation between carotenoid content of ripe yellow tomatoes of different varieties and Raman count (bar box) of the tomato recorded at 488 nm excitation.

The Raman measurements did not require any preparation procedures with the exception of bringing the samples into contact with the window of the optical probe head (see FIG. 2). FIG. 9 shows the results correlating HPLC and Raman detection of carotenoids in a number of tomato extracts. Clearly, the levels determined by Raman spectroscopy correlate very well with carotenoid levels determined by HPLC. Similarly, we observed that different varieties of tomatoes at the same stage of ripeness showed a direct correlation between carotenoid content (μg/g) and Raman count irrespective of color (FIGS. 10–12). As seen from Tables 2A and 2B, the correlation between Raman and HPLC varies with the vegetable and carotenoid content.

TABLE 2A

| | | VEGETABLES | | | | |
| --- | --- | --- | --- | --- | --- | --- |
| | Raman | Carotenoid content (μg/g) | | | | Total |
| Vegetables | reading at 488 nm | Lutein | Zeaxanthin | Carotene | Lycopene | (μg/g) |
| Red Tomato (Roma) | 4294 | 32 | 12 | 410 | 1986 | 2440.0 |
| Red Tomato (German) | 14562 | 58 | 6 | 1800 | 2462 | 4326.0 |
| Peppers | | | | | | |
| Red | 25019 | 46 | 280 | 51 | — | 377 |
| Orange | 61750 | 27 | 652 | 32 | — | 711 |

TABLE 2A-continued

VEGETABLES

| Vegetables | Raman reading at 488 nm | Carotenoid content (µg/g) | | | | Total (µg/g) |
| --- | --- | --- | --- | --- | --- | --- |
| | | Lutein | Zeaxanthin | Carotene | Lycopene | |
| Yellow | 88115 | 165 | 310 | 230 | — | 705 |
| Green | | | | | | |
| a. Light | 59202 | 58 | 25 | 12 | | 95 |
| b. Dark | 57259 | 52 | 29 | 10 | | 91 |
| Carrot | 23387 | 260 | — | 17000 | — | 17260 |
| Green leafy vegetables | | | | | | |
| Spinach leaf | 57788 | 299.3 | 41.7 | 32.3 | | 372 |
| Lettuce leaf | 93905 | 102.3 | 341.2 | 56.0 | | 499 |
| Beet leaf | 96913 | 342.7 | 136.0 | 47.4 | | 525 |

TABLE 2B

FRUIT JUICES
Raman reading and HPLC carotenoid content of fruit juices

| Fruits | Absorbance | | Raman reading | | Carotenoid content (µg/100 ml) | | | | Total (µg/100 ml) |
| --- | --- | --- | --- | --- | --- | --- | --- | --- | --- |
| | 488 | 515 | 488 | 515 | Lutein | Zeaxanthin | β-Carotene | Lycopene | |
| tomato | ∞ | ∞ | 17035 | 7000 | 32 | 39.8 | 108 | 1270 | 1449.8 |
| 1:10 dil* | 1.25 | 1.25 | 3306 | 825 | 2 | 3 | 9 | 211.0 | 225.3 |
| berry | 0.50 | 0.49 | 470 | 53 | nd | nd | 5 | nd | 5 |
| 1:10 dil | 0.06 | 0.06 | 0 | 100 | nd | nd | 0.5 | nd | 0.5 |
| Carrot | ∞ | ∞ | 12476 | 21053 | 283 | 36.6 | 1259 | nd | 1578.6 |
| 1:10 dil | 1.20 | 1.10 | 5660 | 2619 | 29 | 4 | 530 | nd | 563.0 |
| Red grape | 1.90 | 1.90 | 300 | 29 | nd | nd | 12 | nd | 12 |
| 1:10 dil | 0.19 | 0.18 | 33 | 32 | nd | nd | 1.09 | nd | 1 |
| orange | ∞ | ∞ | 8504 | 1400 | 6 | 18 | 512 | nd | 536 |
| 1:10 dil | 0.9 | 0.8 | 1176 | 282 | — | 1 | 71.2 | nd | 72.2 |
| Veg mix | ∞ | ∞ | 23050 | 9000 | 14 | 7.4 | 229 | 1786 | 2036.4 |
| 1:10 dil | 1.1 | 1.05 | 2297 | 941 | 1.2 | 7.0 | 26 | 175 | 209.2 |

*Diluted in distilled water;
nd; not detected

As seen in Table 2B the decrease in the carotenoid content due to dilution was directly related to the decrease in the Raman count. These results demonstrate an excellent experimental correlation (R=0.96) between HPLC data and Raman data for 9-fold diluted juices, including good correlation (R=0.93) even for raw (undiluted, from a can) juices.

We claim:

1. A method of evaluating an agricultural product as a prerequisite to further action, comprising the steps of:
   exposing the agricultural product to a laser beam having a nominal wavelength;
   collecting light scattered by the product;
   analyzing the light scattered by the product to identify a wavelength shift characteristic of a carotenoid;
   determining the concentration level of the carotenoid within the agricultural product;
   wherein the agricultural product is a processed food product made from post-harvest fruits or vegetables; and
   classifying the agricultural product as desirable or undesirable as a function of the concentration level.

2. A method of evaluating an agricultural product as a prerequisite to further action, comprising the steps of:
   exposing the agricultural product to a laser beam having a nominal wavelength;
   collecting light scattered by the product;
   analyzing the light scattered by the product to identify a wavelength shift characteristic of a carotenoid;
   determining the concentration level of the carotenoid within the agricultural product;
   wherein the agricultural product is being processed into a food product made from post-harvest fruits or vegetables; and
   classifying the agricultural product as desirable or undesirable as a function of the concentration level.

3. A method of evaluating an agricultural product as a prerequisite to further action, comprising the steps of:
   exposing the agricultural product to a laser beam having a nominal wavelength;
   collecting light scattered by the product;
   analyzing the light scattered by the product to identify a wavelength shift characteristic of a carotenoid;
   determining the concentration level of the carotenoid within the agricultural product;
   wherein the agricultural product is a packaged food product; and
   classifying the agricultural product as desirable or undesirable as a function of the concentration level.

4. A method of evaluating an agricultural product as a prerequisite to further action, comprising the steps of:
   exposing the agricultural product to a laser beam having a nominal wavelength;

collecting light scattered by the product;
analyzing the light scattered by the product to identify a wavelength shift characteristic of a carotenoid;
determining the concentration level of the carotenoid within the agricultural product;
wherein the agricultural product is within a crop or forest; and
classifying the agricultural product as desirable or undesirable as a function of the concentration level.

5. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the level of the carotenoid is used to determine plant heath or stress; and
classifying the agricultural product as desirable or undesirable as a function of the concentration level.

6. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the carotenoid is beta-carotene, lutein, violaxanthin, neoxanthin, antheraxanthin or zeaxanthin; and
classifying the agricultural product as desirable or undesirable as a function of the concentration level.

7. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
analyzing the light scattered by the product to identify a wavelength shift characteristic of terpenes, polyenes, chlorophyll, proteins, starches, sugars, overall nitrogen levels, flavonoids, or vitamins; and
classifying the agricultural product as desirable or undesirable as a function of the concentration level.

8. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the concentration level of the carotenoid is determined through comparison with an external standard; and
classifying the agricultural product as desirable or undesirable as a function of the concentration level.

9. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the concentration level of the carotenoid determined through comparison with another substance present in the agricultural product; and
classifying the agricultural product as desirable or undesirable as a function of the concentration level.

10. A method of evaluating an agricultural product as a prerequisite to further action, comprising the steps of;
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the concentration level of one carotenoid is determined through comparison with another cartenoid; and
classifying the agricultural product as desirable or undesirable as a function of the concentration level.

11. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the agricultural product is a leafy plant, and the method includes the steps of:
determining a level of chlorophyll;
determining the stress of the plant from a leaf carotenoid to chlorophyll ratio; and
classifying the agricultural product as desirable or undesirable as a function of the concentration level.

12. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
determining a level of the cartenoid violaxanthin;
determining a level of the cartenoid antheraxanthin or zeaxanthin;
assessing one or more environmental effects by comparing the level of violaxanthin to the level of antheraxanthin or zeaxanthin; and
classifying the agricultural product as desirable or undesirable as a function of the concentration level.

13. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;

determining the concentration level of the carotenoid within the agricultural product;
exposing the agricultural product to multiple laser beams; wherein some or all of the nominal wavelengths are different; and
classifying the agricultural product as desirable or undesirable as a function of the concentration level.

14. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
performing a time-dependent analysis on the detected scattered light; and
classifying the agricultural product as desirable or undesirable as a function of the concentration level.

15. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
providing portable apparatus operative to generate the laser beam and collect the light scattered by the agricultural product; and
classifying the agricultural product as desirable or undesirable as a function of the concentration level.

16. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product; and
taking remedial action in conjunction with the determined concentration level of the carotenoid.

17. The method of claim 16, wherein the remedial action includes watering, fertilizing or the application of a herbicide or insecticide.

18. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product; and
using the level of the carotenoid as part of a plant breeding or genetic engineering program.

19. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
determining the geographic position of the agricultural product; and
classifying the agricultural product as desirable or undesirable as a function of the concentration level.

20. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
determining the distance to the agricultural product; and
classifying the agricultural product as desirable or undesirable as a function of the concentration level.

21. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the step of analyzing the light scattered by the product is analyzed in conjunction with a remote sensing technique; and
classifying the agricultural product as desirable or undesirable as a function of the concentration level.

22. The method of claim 21, wherein the remote sensing technique includes one or more of the following:
Raman spectroscopy, fluorescence, ultraviolet spectra, infrared spectra or emission, ultrasound, visual appearance, or smell.

23. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the step of analyzing the light scattered by the product is analyzed in conjunction with an invasive analysis technique; and
classifying the agricultural product as desirable or undesirable as a function of the concentration level.

24. The method of claim 23, wherein the invasive analysis technique includes one or more of the following:
touch, HPLC or other chromatography, or consumption by a human, animal or bacteria.

25. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
removing a portion of an outer covering of the agricultural product;

exposing the removed portion or the vacancy left by the removed portion of the agricultural product to the laser beam; and classifying the agricultural product as desirable or undesirable as a function of the concentration level.

26. The method of claim 25, wherein the removed portion is a rind, bark or skin.

27. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the step of determining the concentration level of the carotenoid forms part of a freshness evaluation method associated with a produce display; and
classifying the agricultural product as desirable or undesirable as a function of the concentration level.

28. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
characterizing one or more neutraceuticals within the product; and
classifying the agricultural product as desirable or undesirable as a function of the concentration level.

29. A method of evaluating an agricultural product as a prerequisite to further action, comprising the steps of:
exposing the agricultural product to a laser beam having a nominal wavelength;
collecting light scattered by the product;
analyzing the light scattered by the product to identify a wavelength shift characteristic of a carotenoid;
determining the concentration level of the carotenoid within the agricultural product;
wherein the product is a processed or functional food; and
classifying the agricultural product as desirable or undesirable as a function of the concentration level.

30. The method of claim 29, wherein the processed or functional food is a jam, preserve, pet food, baby food, vitamin product, tomato product or dietary supplements.

* * * * *

UNITED STATES PATENT AND TRADEMARK OFFICE
CERTIFICATE OF CORRECTION

PATENT NO. : 7,215,420 B2
APPLICATION NO. : 10/472010
DATED : May 8, 2007
INVENTOR(S) : Werner Gellerman et al.

It is certified that error appears in the above-identified patent and that said Letters Patent is hereby corrected as shown below:

On Title Page, Item 60, Domestic Priority omitted, -- 60/278,055, filed 03/22/2001 --

Column 10, line 5, replace, "Easer radiation" with -- laser radiation --

Column 10, line 30, delete "to"

Column 12, table 2A, replace "Raman" with -- Raman reading at 488 nm --

Signed and Sealed this

Sixteenth Day of October, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,215,420 B2 |
| APPLICATION NO. | : 10/472010 |
| DATED | : May 8, 2007 |
| INVENTOR(S) | : Werner Gellerman et al. |

Page 1 of 1

It is certified that error appears in the above-identified patent and that said Letters Patent is hereby corrected as shown below:

Title Page, Item 60 Domestic Priority omitted, add -- 60/278,055, filed 03/22/2001 --

Column 10, line 5, replace , "Easer radiation" with -- laser radiation --

Column 10, line 30, delete "to"

Column 12, table 2A, replace "Raman" with -- Raman reading at 488 nm --

Column 15, line 20, replace "heath" with -- health --

Signed and Sealed this

Third Day of June, 2008

JON W. DUDAS
*Director of the United States Patent and Trademark Office*